United States Patent [19]

Doan et al.

[11] Patent Number: 5,354,328
[45] Date of Patent: Oct. 11, 1994

[54] PATCH ELECTRODE FOR AN IMPLANTABLE DEFIBRILLATOR

[75] Inventors: Phong D. Doan, Stevenson Ranch; Gabriel Mouchawar, Newhall; James D. Causey, III, Simi Valley, all of Calif.

[73] Assignee: Siemens Pacesetter, Inc., Sylmar, Calif.

[21] Appl. No.: 5,694

[22] Filed: Jan. 19, 1993

[51] Int. Cl.$^5$ ............................................. A61N 1/05
[52] U.S. Cl. ................................................... 607/129
[58] Field of Search ......................................... 607/129

[56] References Cited

U.S. PATENT DOCUMENTS

| | | |
|---|---|---|
| D. 273,514 | 4/1984 | Heilman et al. . |
| D. 274,514 | 4/1984 | Hellman et al. ............... 607/129 |
| 4,030,509 | 6/1977 | Heilman et al. . |
| 4,291,707 | 9/1981 | Heilman et al. ............... 607/129 |
| 4,314,095 | 2/1982 | Moore et al. . |
| 4,628,937 | 12/1986 | Hess et al. . |
| 4,827,932 | 5/1989 | Ideker et al. . |
| 4,938,231 | 7/1990 | Milijasevic et al. . |
| 5,042,463 | 8/1991 | Lekholm ............................ 607/129 |

OTHER PUBLICATIONS

"*Electrosurgery*", John A. Pearce, PhD, pp. 156–158.
"*Clinical Results with the Tachylog Antitachycaria Pacemaker*", Edgar Sowton, pp. 1313–1317.

Primary Examiner—William E. Kamm
Assistant Examiner—Scott M. Getzow
Attorney, Agent, or Firm—Lisa P. Weinberg

[57] ABSTRACT

A patch electrode including a generally oval-shaped metallic mesh affixed to a polymer insulation backing and an insulation frame, and further including a plurality of specially designed lattices which divide the metallic mesh into a plurality of windows or apertures. The windows effectively act as smaller electrodes distributing the higher current densities inward from each of their own individual edges.

27 Claims, 2 Drawing Sheets

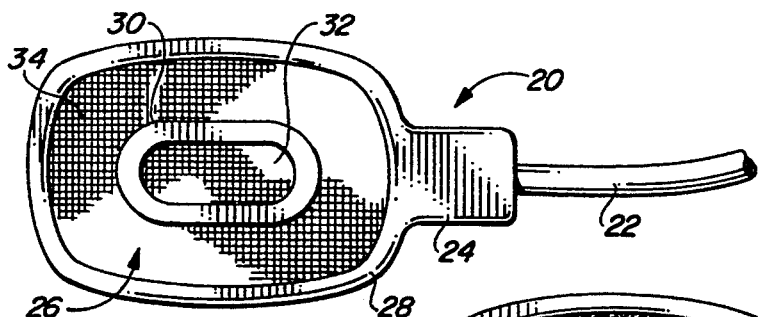
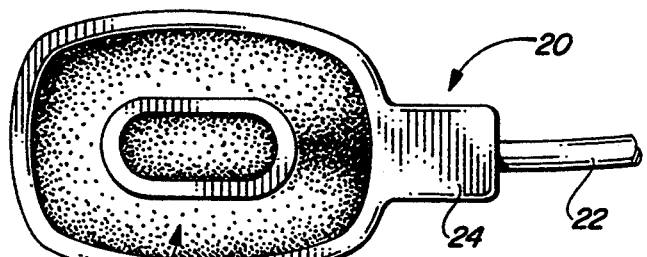
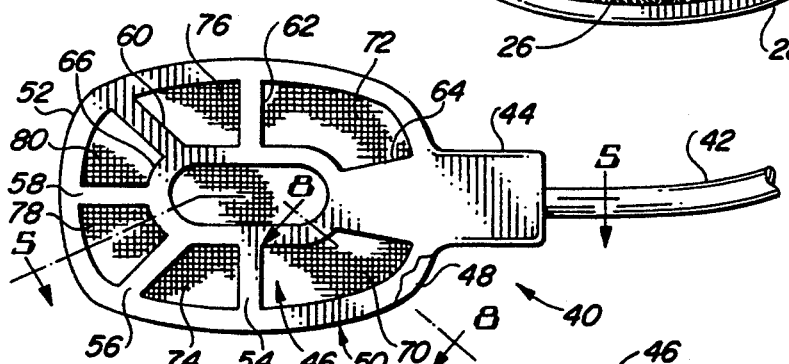
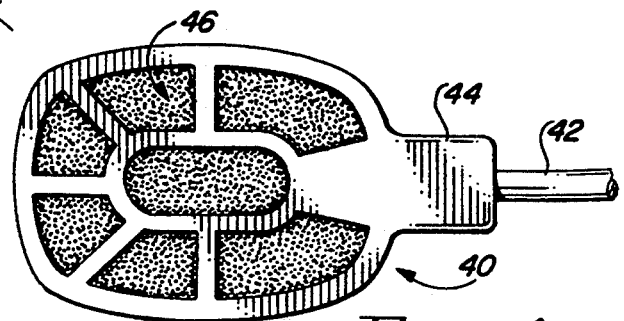
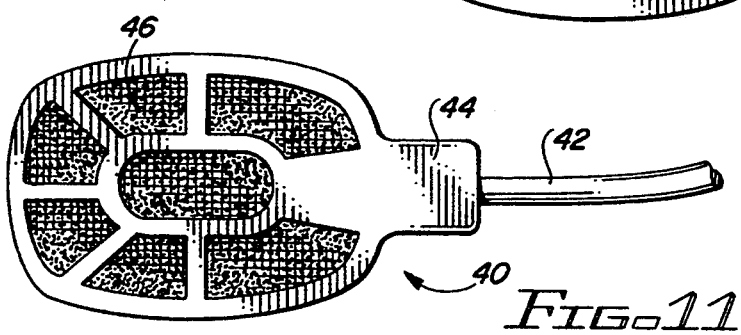
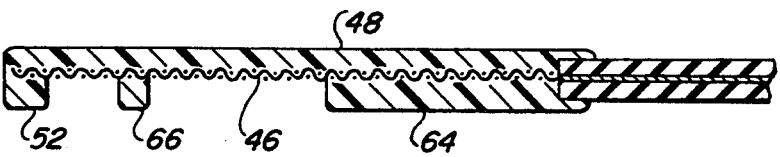

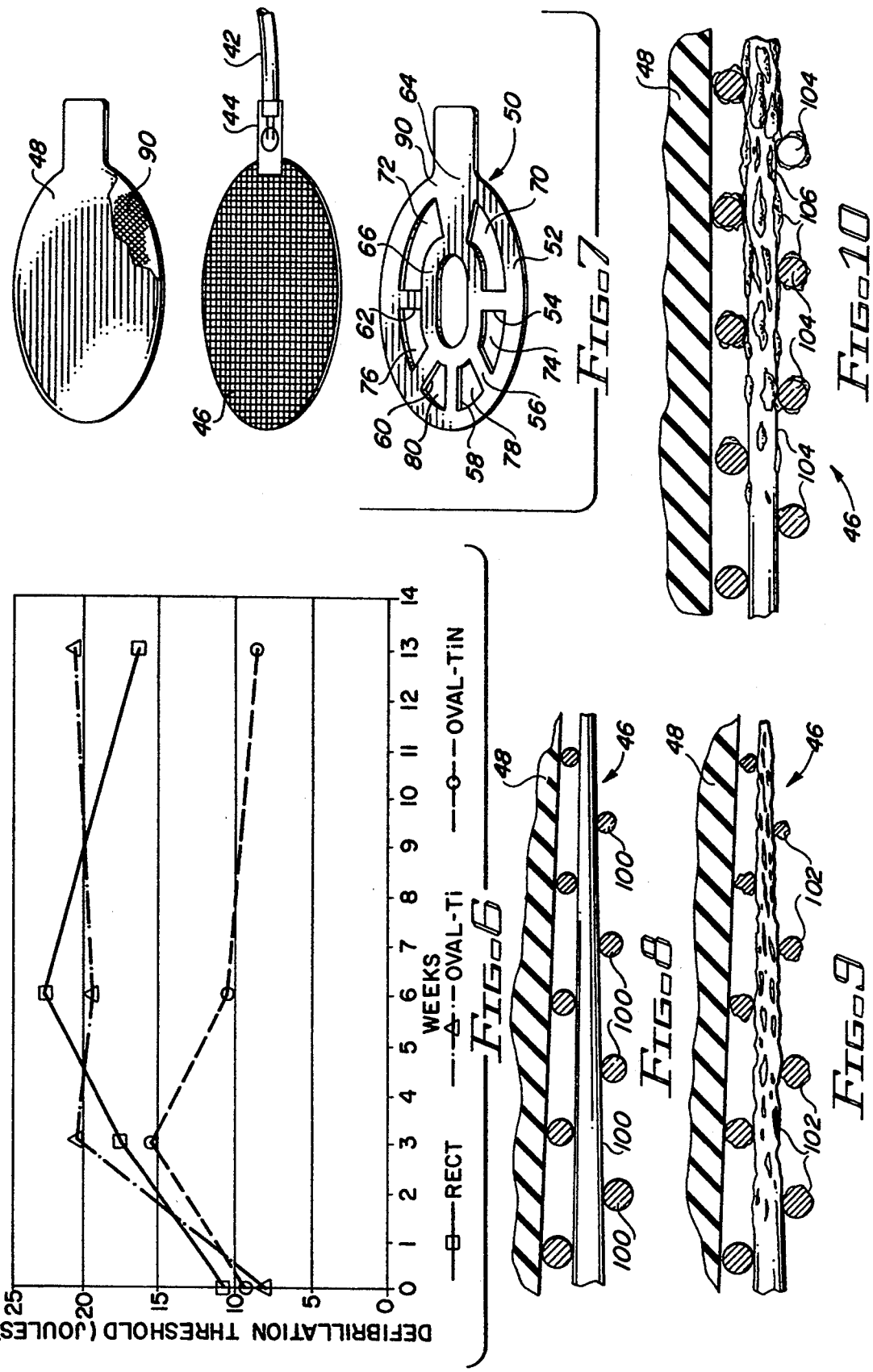

PATCH ELECTRODE FOR AN IMPLANTABLE DEFIBRILLATOR

BACKGROUND OF THE INVENTION

The present invention is directed to the design of an implantable defibrillator patch electrode for use with a cardiac pacing and defibrillating device. More particularly, the present invention is directed to the design of patch electrodes which are secured to the exterior surface of the heart to deliver an electrical stimulus to the heart to cause defibrillation.

Tachycardia is a condition in which the atria, ventricles or both chambers of the heart, beat very rapidly, and not within the normal physiological range, typically exceeding 160 occurrences per minutes. Atrial tachycardia is the medical term assigned to the condition in which rapid and regular succession of P-waves of the PQRST waveform complex occur. The rate of occurrence is in excess of the physiological range normally encountered in the particular patient.

Paroxysmal supra-ventricular tachycardia is the medical term assigned to the condition in which there is a sudden attack of rapid heart condition in the atria or in the atrial-ventricular node. The characteristics are generally the same as those in atrial tachycardia.

Normally atrial tachycardia and paroxysmal supra-ventricular tachycardia are not a life-threatening condition, unless they progress into ventricular tachycardia or fibrillation. Ventricular tachycardia is the medical term assigned to the condition in which rapid and regular succession of R-waves of the QRST waveform complex occur. Again, the rate of occurrence is in excess of the physiological range of the particular patient and, if left untreated, can progress into ventricular fibrillation. In ventricular fibrillation, the ventricles are unable to pump blood in a coordinated fashion and cardiac output drops to a level dangerous to the patient.

Typically, these life-threatening conditions of ventricular tachycardia or ventricular fibrillation must be treated by drug therapy or by electrical stimulation, such as cardioversion or defibrillation. Implantable defibrillators have been developed to monitor the pacing of the heart, and provide a defibrillation charge via an electrode attached to or implanted in the heart. These implantable defibrillators allow the recipient a considerable degree of freedom to pursue normal activities with the defibrillator monitoring the rate of the heart and providing a defibrillation charge immediately upon onset of ventricular tachycardia.

Accordingly, for certain patients, it is beneficial to affix to the exterior surface of the cardiac muscle a patch electrode which, when electrically connected to an electrical power source, can deliver a large electrical stimulus directly to the cardiac muscle to cause defibrillation. The electrical energy necessary for defibrillation when delivered by an implanted patch electrode may be in the range of, for example, between 1 and 100 joules, but is preferably in the range of between 5 and 30 joules. It is important to recognize that when this amount of energy is being coupled directly to the cardiac muscle, there is a potential for severe damage to the tissue. If such damage occurs, the efficiency of the defibrillation for the patch electrode in a subsequent application may be severely impaired.

In addition, the design of the patch electrode must allow intimate contact over a substantial surface of the cardiac muscle and effective delivery of the defibrillation energy. A further consideration of the design of the patch electrode requires, given its location on the surface of the continuously flexing cardiac muscle, that the patch electrode itself is extremely flexible and resistant to fatigue.

With the foregoing in mind, a patch electrode is normally designed as a metallic mesh positioned between a polymer insulating backing and an insulating frame. The patch shapes which have been used include both oval shapes and rectangular shapes. Generally, an oval shape allows more intimate contact with the surface of the heart muscle. The insulating backing is bonded to the metallic mesh and operates to direct the defibrillation current toward the opposite side of the patch electrode, into the cardiac muscle. One problem associated with bonding the wire mesh of the electrode to the insulating backing is the potential for delamination and associated tissue ingrowth. One design which reduces this problem on a rectangular patch is illustrated in Design Patent No. 273,514, wherein the rectangular patch electrode is overlaid with an insulating lattice which divides the rectangular patch electrode into six squares. The lattice may assist in preventing delamination between the insulating backing and the wire mesh of the patch electrode.

A common problem with metallic patch electrodes is the high current density around the perimeter which may be referred to as fringing or edge effect. This effect can cause an uneven current distribution to the cardiac muscle, resulting in high defibrillation threshold levels and tissue damage proximate the edge of the patch electrode. It would therefore be desirable to provide an even current or polarization distribution for a patch electrode.

SUMMARY OF THE INVENTION

The present invention defines an enhanced design for a patch electrode for use with an implantable defibrillator. The lattices are silicone insulation material which permeate through the electrode mesh and bond to the backing insulation material. This configuration provides two beneficial effects. First, the patch has a larger perimeter than a standard oval electrode. The larger perimeter on the electrode causes the defibrillation current to be effectively spread out over a longer edge of the electrode, and thus the current is more evenly coupled to the cardiac muscle. In addition, the magnitude of the defibrillation level is decreased by effective utilization and distribution of the defibrillation current. The second primary benefit to the design of the lattice in segregating the individual windows is the reduced delamination of the wire mesh from the insulation backing, and thereby a reduction in the amount of tissue ingrowth into and through the mesh and between the mesh and the insulation backing.

BRIEF DESCRIPTION OF THE DRAWINGS

FIG. 1 depicts the standard design for a patch electrode according to the prior art;

FIG. 2 depicts the patch electrode of FIG. 1 and the fringing or edge effect for the electrical current distribution;

FIG. 3 depicts a patch electrode according to the present invention;

FIG. 4 depicts the patch electrode of FIG. 3 and illustrates the current distribution which results from the modified design;

FIG. 5 depicts a cross-sectional view of the patch electrode of FIG. 3 along line 5—5 of FIG. 3;

FIG. 6 is a graphical representation of defibrillation threshold as a function of implant time for alternative patch electrode designs;

FIG. 7 is an exploded view showing the components of the patch electrode of FIG. 3.

FIG. 8 depicts an alternative embodiment depicted in a partial cross-sectional view taken along segment 8—8 of FIG. 3;

FIG. 9 depicts an alternative embodiment depicted in a partial cross-sectional view taken along segment 8—8 of FIG. 3;

FIG. 10 depicts an alternative embodiment depicted in a partial cross-sectional view taken along segment 8—8 of FIG. 3; and FIG. 11 depicts the patch electrode of FIG. 3 modified with the alternative embodiments of one of FIGS. 8, 9 or 10 and illustrates the current distribution which results from the modified alternative design.

DETAILED DESCRIPTION OF THE PREFERRED EMBODIMENT

FIG. 1 depicts a patch electrode 20 attached to a conductor 22 which is also interconnected to an implanted defibrillator (not shown) which includes a power source. The patch electrode 20 is attached to the conductor 22 at a connecting portion 24. As depicted, the patch electrode 20 includes a generally oval-shaped wire mesh 26 which is bordered by an insulation rim 28. The patch electrode 20 may also include a generally oval-shaped reinforcing ridge 30, which segregates the wire mesh 26 into an internal portion 32 and a generally oval or racetrack-shaped portion 34.

In FIG. 2, the patch electrode 20 of FIG. 1 is again depicted, and the exposed areas of the wire mesh which are shaded illustrate the locations of the concentration of the current density, i.e., the locations of the edge effect. The current density tends to concentrate near the outer periphery of the wire mesh 26, close to the insulation rim 28. In addition, high current densities are located in the area of the wire mesh 26 immediately adjacent the interconnection to the electrical conductor 22. The net result of the concentration of current density is that a majority of the effective current is distributed to a smaller surface area of the heart, and the electrical energy required to successfully defibrillate is necessarily higher.

FIGS. 3 and 4 depict a patch electrode 40 according to the present invention. As in the prior design, the patch electrode 40 is connected by a conductor 42 to a implantable defibrillator (not shown) having a power source. The point of connection of the patch electrode 40 and the electrical conductor 42 is shown at attachment element 44. The patch electrode 40 includes a generally oval-shaped wire mesh 46 sandwiched between an insulating backing sheet 48 and a facing sheet 50. The facing sheet 50 preferably includes an outer rim 52 defining a generally oval shape slightly larger than and overlapping the outer edge of the wire mesh 46.

The facing sheet 50 also includes a plurality of lattice elements 54, 56, 58, 60 and 62 as well as a generally wedge-shaped element 64, each of which converges radially inward from the outer rim 52 to a central oval 66. The lattice elements 54, 56, 58, 60 and 62 and the wedge-shaped element 64, combine to segregate the wire mesh 46 into a plurality of windows 70, 72, 74, 76, 78 and 80. The purpose of segregating the patch electrode 40 into the plurality of windows 70–80, is to increase the electrode perimeter, thereby providing a more even distribution of the current density delivered over the exposed surface of the patch electrode 40.

The lattice elements 54–62, are preferably positioned such that the surface area for the respective windows 70–80 decreases with increasing distance from the point of connection with the electrical conductor 42. Thus, as depicted in FIG. 3, the windows 70 and 72 have the largest surface area and are located closest to the electrical conductor 42. Windows 74 and 76 have a surface area which is smaller than that of windows 70 and 72, while the windows 78 and 80 have a surface area which is smaller than the surface area of windows 74 and 76. Therefore, windows 78 and 80 will have a higher perimeter to area ratio as compared to windows 74 and 76. Windows 78 and 80 are located farthest from the point of interconnection with the conductor 42.

By configuring the windows 70–80 to have a decreasing surface area and an increasing perimeter to area ratio with increasing distance from the point of interconnection with the conductor 42, the current density is more effectively spread out over each of the respective windows. The reason is that the apportioned quantums of current is greater for the windows closest to the point of connection with the electrical conductor 42, yet it is spread over a greater surface area as it propagates toward the edges of the larger windows 70 and 72. Window 74 and 76, which are spaced farther from the point of connection to the conductor 42, are apportioned respectively higher quantums of current than windows 78 and 80. Again however, because of their greater surface area, the current density is evenly distributed. Thus, the overall effect is that the defibrillation current density is more uniformly spread out over the entire surface area of the patch electrode 40. This effect is illustrated in FIG. 4, wherein the distribution of the current density is shown by a generally uniform shading of the wire mesh 44 portion of the patch electrode 40.

The components of the facing sheet 50, including the outer rim 52, lattice elements 54–62, wedge-shaped insulation element 64, and central oval 66 are preferably formed from a silicone pattern which is laid over the surface of the oval-shaped wire mesh 46 and then bonded to the wire mesh 46 by the application of heat and pressure. In addition, the silicone penetrates the mesh and bonds to the backing sheet 48, as shown in the cross-sectional view of FIG. 5.

The combined effect of the lattice elements 54–62 and the outer rim 52, as well as the wedge-shaped insulation element 64, also increases the mechanical bond between the wire mesh and the backing sheet 48. This enhancement of the mechanical bonding decreases the possibility of delamination between the wire mesh 46 of the patch electrode and the backing sheet 48. By decreasing the possibility of delamination, the opportunity for tissue ingrowth into the areas between the individual wires of the wire mesh 46, and more particularly between the wire mesh 46 and the backing sheet 48, is substantially decreased. This is beneficial whenever the patch electrode 40 must be removed from the patient's heart to replace a defective patch or to allow other surgical procedures.

The metallic mesh 46 of the patch electrode 40 is preferably formed from titanium wires and may include a titanium nitride coating deposited on the surfaces of the wires. While bare titanium wires have demonstrated satisfactory current delivery, the defibrillation threshold is substantially decreased by the use of the titanium nitride coating on the titanium wires. This effect is illustrated in the graph of FIG. 6, wherein the defibrillation threshold in joules is plotted on the y-axis and the implant time in weeks is plotted on the x-axis.

The patch electrode 40 is illustrated in an exploded view in FIG. 7 wherein the backing sheet 48 is separated from the wire mesh 46 and the facing sheet 50. The facing sheet 50 is preferably formed from a sheet of silicone which is cut to define the outer rim 52, lattices 54–62, central oval 66, and wedge-shaped insulation element 64, as well as a portion of the connector element 44, are also illustrated exploded away from the face of the wire mesh 46.

The backing sheet 48 and facing sheet 50 may be formed from silicone sheets or alternatively from other biocompatible flexible plastics or elastomeric materials. Preferably, however, both the facing sheet 50 and the backing sheet 48 are formed from fabric reinforced silicone sheets. The fabric reinforcement 90 may be a natural fiber such as cotton or silk, or an artificial fiber such as nylon or rayon.

Preferably, the facing sheet 50 and backing sheet 48, including the fabric reinforcement 90 are procured in an unvulcanized state, cut to size, and sandwiched about the pre-cut wire mesh 46. The assembly is then interbonded by the application of pressure and heat to cause the silicone to invade the open spaces of the wire mesh 46, bond to the wire mesh 46, and cure to the vulcanized state.

Alternatives to the configuration of FIG. 3 and 4, which have the ability to provide the desired function, i.e., to evenly distribute the current density over a greater surface area, are accomplished by constructing the patch electrode 40 so that the individual wires of the wire mesh 46 have a resistance which varies depending on the distance from the point of connection 44 to the conductor 42 and from the center of the wire mesh 46.

Thus, for example, the diameters of the individual wires of the wire mesh 46 may be changed either by forming the wire mesh 46 of a specially designed screen, or by taking a generally oval-shaped wire mesh and etching the mesh with an acid, or by incorporating impurities into the material of the individual wires. Alternatively, the ability to deliver the defibrillation charge can be modified by selectively coating portions of the wire mesh in a pattern which causes the current to be distributed over a greater surface area. The first alternative configuration is illustrated in FIG. 8, which shows a cross-sectional view of patch electrode 40 through a portion of the wire mesh 46 of FIG. 3 identified by the lines 8—8.

In FIG. 8, it can be seen that the diameters of the individual wires 100 are illustrated as decreasing toward the radially outer edges of the patch electrode. Alternatively, as illustrated in FIG. 9, which is another alternative view along the same portion of the patch electrode 40 as in FIG. 8, the individual wires 102 have been corroded or etched by an acid bath. FIG. 10 depicts a cross-sectional portion of the patch electrode 40 similar to the portion shown in FIGS. 8 and 9, wherein a surface coating 106 has been selectively sputtered onto the facing surface and individual wires 104 of the wire mesh 46 to form an insulation pattern on the surface of the wire mesh 46. The insulation pattern is denser near the outer edges of the patch electrode and becomes sparser progressing radially inward toward the center of the patch electrode 40. Each of these alternatives improves the distribution of the current density over a greater percentage of the exposed area of the patch electrode 40.

As a further alternative or improvement, any of the three foregoing effects detailed in FIGS. 8, 9 and 10 may be incorporated into the design of the wire mesh 46 with respect to the proximity to the connection 44 with the electrical conductor 42. Thus, the tendency for higher current densities near the connection 44 with the electrical conductor 42 is effectively minimized by the selective altering of the electrical resistance (or by providing the selective coating insulation) of the wires proximate to the connection 44 to the electrical conductor 42.

Any of the design and effects detailed in FIGS. 8, 9 and 10 can be advantageously incorporated not only into the designs of FIGS. 3 and 4, but alternatively also into the design of the prior art patch electrodes illustrated in FIGS. 1 and 2. A charge distribution representation of a patch electrode incorporating these features into a design as shown in FIG. 3, is illustrated in FIG. 11. As can be seen from the uniform distribution of the shading in this example, the edging or fringe effect of the concentration of the current distribution is eliminated by incorporation of the concepts illustrated in FIGS. 8, 9 and 10.

Thus, it may be appreciated that while the preferred method of embodying the concept of the present invention, which is to design a patch electrode which effectively spreads the current distribution over the entire surface of the patch electrode, is accomplished by the lattice and window construction illustrated in FIGS. 3 and 4, the performance of a patch electrode may be enhanced by distributing the current over a greater surface area by the designs illustrated in FIGS. 8, 9 and 10.

According to the foregoing detailed description, the present invention contemplates a method of forming a patch electrode for use with an implantable defibrillator. The patch electrode is formed by forming a generally oval-shaped wire mesh and attaching it to an electrical conductor. A generally oval-shaped insulation backing element is bonded to one surface of the wire mesh, and a facing sheet of insulation material including a peripheral rim portion matching a peripheral edge of the backing sheet is bonded to the opposite side of the wire mesh and also to the backing sheet. The facing sheet preferably includes a plurality of lattice elements converging radially inward from the peripheral rim to define a plurality of windows of exposed wire mesh. The wire mesh is preferably formed from titanium nitride coated titanium wires, while the backing sheet and the facing sheet are formed from a silicone, rubber or plastic material, which may include a fabric reinforcing layer.

The method of forming the patch electrode may further include one or more of the steps of: configuring the wires of the wire mesh to have diameters which decrease near the periphery of the oval, whereby their resistance increases near the periphery of the oval; etching the wires of the wire mesh in a pattern such that their resistance increases near the periphery of the oval; or sputter coating an insulating material on the wires of the wire mesh in a graduated pattern such that the density of the coating increases with increasing radius from the center of the wire mesh.

The present invention also contemplates a method of defibrillating the heart of a patient who has an implanted defibrillator including a power source capable of providing a defibrillation charge. The contemplated method includes forming a shaped wire mesh, and affixing the wire mesh to one end of an electrical conductor, the other end of which is connected to the defibrillator. A backing sheet of biocompatible insulating material is bonded to one surface of the wire mesh, and a facing sheet is bonded to an opposite surface, thereby partially exposing the wire mesh. The patch electrode is attached to the heart, with the partially exposed wire mesh in intimate contact with the heart. When defibrillation is required, a defibrillation stimulus from the power source of the defibrillator is coupled to the heart through the exposed wire mesh of the patch electrode. The facing sheet causes the defibrillation current to be distributed in a generally uniform manner over the entire exposed surface area of the wire mesh, thereby efficiently defibrillating the patient.

It should be evident from the foregoing description that the present invention provides many advantages in the field of implanted defibrillation and patch electrodes. Although a number of preferred and alternative embodiments are specifically illustrated and described herein, it will appreciated that many modifications and variations of the present invention are possible in light of the above teaching to those skilled in the art. It is preferred, therefore, that the present invention be limited not by the specific disclosure herein, but only by the appended claims.

What is claimed is:

1. A patch electrode for use with an implantable defibrillator and connected thereto by an electrical conductor, said patch electrode comprising:
   a generally oval-shaped wire mesh electrically connected to the electrical conductor;
   a generally oval-shaped insulation backing sheet similarly shaped and slightly larger than said wire mesh bonded to one side of said wire mesh; and
   a facing sheet of insulation material bonded to an opposite side of said wire mesh, said facing sheet including a peripheral rim portion matching a peripheral edge of said backing sheet, said facing sheet further including a plurality of lattice elements converging radially inward from said peripheral rim to define therebetween a plurality of windows of exposed wire mesh, said windows having varying area and perimeter, wherein the area of said windows decreases and the perimeter to area ratio increases with increasing distance from the point of connection of said wire mesh with the conductor.

2. The patch electrode of claim 1, wherein said wire mesh is formed from titanium wires and said facing sheet and said backing sheet are formed from silicone sheets.

3. The patch electrode of claim 2, wherein said titanium wires are coated with a titanium nitride coating.

4. The patch electrode of claim 2, wherein said silicone facing sheet and said backing sheet include an embedded fabric reinforcing layer.

5. The patch electrode of claim 4, wherein said fabric reinforcing layer of said facing sheet and said backing sheet is a woven sheet of fibers selected from the group of fibers consisting of natural fibers and artificial fibers, wherein said fibers are flexible and capable of bonding to the silicone of said facing and backing sheets.

6. A patch electrode for use with an implantable power source and interconnected thereto by an electrical conductor, said patch electrode comprising:
   a shaped wire mesh, said wire mesh electrically connected to the conductor;
   a backing sheet of biocompatible insulating material bonded to one surface of said wire mesh, the other surface of said wire mesh being exposed; and
   means for distributing an electrical current in a generally uniform manner over the entire exposed surface area of said wire mesh, said means for distributing including means for increasing the resistance of the wire mesh near the periphery of the wire mesh.

7. The patch electrode according to claim 6, wherein the means for distributing comprises an insulating pattern formed on the surface of the wire mesh to increase the effective perimeter length of the electrode.

8. The patch electrode according to claim 6, wherein said means for distributing the electrical current comprises:
   a facing sheet of insulation material, said facing sheet including a peripheral rim portion matching an outer edge of said backing sheet, said facing sheet further including a plurality of lattice elements converging radially inward from said peripheral rim to define a plurality of windows of exposed wire mesh.

9. The patch electrode of claim 8, wherein said wire mesh is formed from titanium wires and said facing sheet and said backing sheet are formed from silicone sheets.

10. The patch electrode of claim 9, wherein said titanium wires are coated with a titanium nitride coating.

11. The patch electrode of claim 8, wherein said lattice elements of said facing sheet define said windows as having varying area, wherein the area of said windows decreases with increasing distance from the point of connection of said wire mesh with the conductor.

12. The patch electrode according to claim 6, wherein said means for increasing the resistance of the wire mesh comprises:
   a plurality of wires having varying diameters, said wires being woven to form said wire mesh so that their diameters decrease near the periphery of said wire mesh, whereby their resistance increases near the periphery of said wire mesh.

13. The patch electrode according to claim 6, wherein said means for increasing the resistance of the wire mesh comprises:
   a plurality of etched wires having varying cross-sectional areas, said wires being woven to form said wire mesh in a pattern such that their cross-sectional area decreases and their resistance increases near the periphery of said wire mesh.

14. The patch electrode according to claim 6, wherein said means for increasing the resistance of the wire mesh comprises:
   an insulating material sputtered on said wire mesh in a graduated pattern such that the density of the insulating material increases with increasing radius from the center of said wire mesh.

15. The patch electrode according to claim 6, wherein:
   said means for distributing the electrical current further includes a facing sheet of insulation material, said facing sheet including a peripheral rim portion matching an outer rim portion of said backing sheet, said facing sheet further including a plurality of lattice elements converging radially inward from said peripheral rim to define a plurality of windows exposing said wire mesh, wherein the area of said windows decreases with increasing distance from the point of connection of said wire mesh with the conductor; and said means for increasing the resistance of the wire mesh further includes variable resistance wires forming said wire mesh, said variable resistance wires either having diameters which decrease near the periphery, or the wires of said wire mesh are etched in a pattern whereby their cross sectional area decreases near the periphery, such that the resistance of the wires increases near the periphery of said wire mesh.

16. The patch electrode of claim 15, wherein said wire mesh is formed from titanium wires having a titanium nitride coating and said facing sheet and said backing sheet are formed from silicone.

17. The patch electrode of claim 6, wherein:

said means for distributing the electrical current further includes a facing sheet of insulation material, said facing sheet including a peripheral rim portion matching the outer rim portion of said backing sheet, said facing sheet further including a plurality of lattice elements converging radially inward from said peripheral rim to define a plurality of windows exposing said wire mesh, wherein the area of said windows decreases with increasing distance from the point of connection of said wire mesh with the conductor; and said means for increasing the resistance of the wire mesh includes an insulating material sputtered on the wires of said wire mesh in a graduated pattern such that the density of the coating increases with increasing radius from the center of said oval.

18. The patch electrode of claim 17, wherein said wire mesh is formed from titanium wires having a titanium nitride coating and said facing sheet and said backing sheet are formed from silicone.

19. A method of forming a patch electrode for use with an implantable defibrillator and connected thereto by an electrical conductor, the method comprising the steps of:

forming a generally oval-shaped wire mesh with an increased resistance near the periphery of said wire mesh;

electrically connecting said wire mesh to an electrical conductor;

bonding a generally oval-shaped insulation backing element to one surface of said wire mesh; and bonding a facing sheet of insulation material including a peripheral rim portion matching a peripheral edge of said backing sheet to said wire mesh and said backing sheet, so that an electrical current is distributed in a generally uniform manner over the entire exposed surface area of said wire mesh.

20. The method of forming a patch electrode according to claim 19, wherein said wire mesh is formed from titanium nitride coated titanium wires and said backing sheet and said facing sheet are formed from a material selected from the group consisting of silicone, rubber and plastic.

21. The method of forming a patch electrode according to claim 19, wherein the step of forming said wire mesh further comprises the step of:

configuring the wires of said wire mesh to have diameters which decrease near the periphery of said oval, whereby their resistance increases near the periphery of said wire mesh.

22. The method of forming a patch electrode according to claim 19, wherein the step of forming said wire mesh further comprises the step of:

etching the wires of said wire mesh in a pattern such that their resistance increases near the periphery of the oval.

23. The method of forming a patch electrode according to claim 19, wherein the step of forming said wire mesh further comprises the step of:

sputter coating an insulating material on the wires of said wire mesh in a graduated pattern such that the density of the coating increases with increasing radius from the center of said wire mesh.

24. A method of forming a patch electrode for use with an implantable defibrillator and connected thereto by an electrical conductor, method comprising the steps of:

forming a shaped wire mesh;

electrically connecting said wire mesh to an electrical conductor;

bonding an insulation backing element to one surface of said wire mesh;

forming a facing sheet with a plurality of windows having varying area, the area of said windows decreasing as the distance from the point of connection with the conductor increases; and bonding said facing sheet to said wire mesh and said backing sheet.

25. The method of forming a patch electrode according to claim 24, wherein the perimeter to area ratio of said windows increases with increasing distance from the point of connection of said wire mesh with the conductor.

26. A patch electrode for use with an implantable power source and interconnected thereto by an electrical conductor, said patch electrode comprising:

a shaped wire mesh, said wire mesh electrically connected to the conductor;

a backing sheet of biocompatible insulating material bonded to one surface of said wire mesh; and a facing sheet of insulation material, said facing sheet including a peripheral rim portion matching an outer edge of said backing sheet, said facing sheet further including a plurality of lattice elements which define a plurality of windows of exposed wire mesh, said windows having varying area, wherein the area of said windows decreases with increasing distance from the point of connection of said wire mesh with the conductor so that an electrical current is distributed in a generally uniform manner over the entire exposed surface area of said wire mesh.

27. The patch electrode according to claim 26, wherein the facing sheet comprises:

an insulating pattern formed on the surface of the wire mesh which increases the effective perimeter length of the electrode, wherein the perimeter to area ratio increases with increasing distance from the point of connection of said wire mesh with the conductor.

* * * * *